United States Patent
Falk et al.

(10) Patent No.: US 7,759,454 B2
(45) Date of Patent: Jul. 20, 2010

(54) PROCESS FOR PREPARING AMIDES BASED ON POLYETHERAMINES AND (METH)ACRYLIC ACID

(75) Inventors: Uwe Falk, Bruchkoebel (DE); Martin Glos, Essen (DE); Roman Morschhaeuser, Mainz (DE); Helmut Ritter, Wuppertal (DE); Sarah Schmitz, Duesseldorf (DE)

(73) Assignee: Clariant Produkte (Deutschland) GmbH, Frankfurt (DE)

( * ) Notice: Subject to any disclaimer, the term of this patent is extended or adjusted under 35 U.S.C. 154(b) by 1113 days.

(21) Appl. No.: 11/404,157

(22) Filed: Apr. 13, 2006

(65) Prior Publication Data

US 2006/0252884 A1 Nov. 9, 2006

(30) Foreign Application Priority Data

Apr. 15, 2005 (DE) .................. 10 2005 017 453

(51) Int. Cl.
*C08G 73/10* (2006.01)
*C08G 73/00* (2006.01)

(52) U.S. Cl. ..................... 528/422; 430/627
(58) Field of Classification Search ................ 528/422; 430/627
See application file for complete search history.

(56) References Cited

U.S. PATENT DOCUMENTS

| | | | |
|---|---|---|---|
| 2,719,177 | A | 9/1955 | Coover |
| 4,206,143 | A | 6/1980 | Wenzel |
| 4,675,442 | A | 6/1987 | Besecke |
| 6,017,426 | A | 1/2000 | Semeria |
| 6,175,037 | B1 | 1/2001 | Tweedy |

OTHER PUBLICATIONS

German Office Action Application DE102005 017453.1, dated Oct. 13, 2005.
Ianelli, M. et al., "Selective microwave-accelerated synthesis and polymerization of chiral methacrylamide . . . ", Tetrahedron, 2005, vol. 61, pp. 1509-1515.
Goretzki, C. et al., "Green Polymer Chemistry: Microwave-Asisted Single-Step Synthesis of Various(Meth)acrylates . . . ", Macromol Rapid Commun., 2004, vol. 25, pp. 513-516.
English Language Abstract of Japanese Patent Publication JP61246157A, (Nov. 1, 1986).
European Office Action—Application EP 06005454.1, dated Aug. 14, 2006.
Vazquez-Tato, M.P., Microwave-Mediated Synthesis of Amides, Synett, Thieme International, 1993, No. 7, p. 506, Stuttgart, Germany.

*Primary Examiner*—Duc Truong
(74) *Attorney, Agent, or Firm*—Tod A. Waldrop

(57) ABSTRACT

The invention provides a process for preparing amides from polyetheramines and (meth)acrylic acid or the corresponding anhydrides, the energy source used being microwaves.

8 Claims, No Drawings

PROCESS FOR PREPARING AMIDES BASED ON POLYETHERAMINES AND (METH)ACRYLIC ACID

The present invention relates to a process for preparing amides of acrylic acid or methacrylic acid with polyetheramines using microwaves as the energy source. The amides thus obtained serve as macromonomers whose properties can be varied by the selection of the suitable polyetheramine.

Polyetheramines contain a polyalkylene glycol group. Depending on which monomers are used to form polyalkylene glycols, different properties can be obtained. For instance, water-soluble compounds are obtained at a high content of polyethylene glycol and water-insoluble compounds when propylene glycols are used. It is also possible to influence their melting point and their viscosity by varying the molar masses of the polyalkylene glycols. The use of different starter alcohols for the alkoxylation allows surfactant properties to be achieved. It is also possible to use polyhydric alcohols to form branched systems which then lead, after aminolysis and amidation, to monomers with crosslinking action. This gives rise to various means of using macromonomers based on polyalkylene glycols to influence, in a controlled manner, the properties of a polymer based thereon.

Among the amides of the olefinically unsaturated carboxylic acids, particularly the (meth)acrylamides are of industrial interest, since they constitute starting compounds for the preparation of polymers and copolymers which find use in various fields. The term (meth)acrylamides represents methacrylamide and acrylamide.

One advantage of the amides over the corresponding esters is the greater stability, which is manifested, for example, by lower hydrolysis sensitivity.

In the preparation of the amides starting from amines with (meth)acrylic acid, various problems are observed. An undesired side reaction is Michael addition of the amines to the double bond of the unsaturated carboxylic acid. Moreover, (meth)acrylic acid derivatives tend to polymerize under the influence of heat or light. In the course of preparation and distillative purification in particular, they are exposed to temperatures which can readily induce undesired polymerization.

The prior art discloses various processes for preparing (meth)acrylamides.

DE-A-28 16 516 describes a process in which (meth)acrylamides are prepared starting from alkyl (meth)acrylates. To prevent Michael adducts, this process is performed in the presence of dibutyltin oxide.

DE-A-31 23 970 describes a process in which (meth)acrylamides are prepared starting from alkyl (meth)acrylates. To prevent Michael adducts, this process is performed in the presence of compounds of metals of transition group 4 and/or compounds of the metals lead, tantallum and/or zinc as catalysts.

EP 0 992 480 A1 describes a process for preparing esters of (meth)acrylic acid using microwaves as an energy source. However, no amides are prepared there by this method.

Of particular interest are macromonomers based on polyalkylene glycols, since the use of hydrophobic and/or hydrophilic alkylene oxides or starting compounds with the appropriate properties in the preparation of the parent polyalkylene glycol allows the hydrophilicity/hydrophobicity of the macromonomer to be influenced in a controlled manner. When polyalkylene glycols are used in chemical reactions, there is often the problem of increased polymerization tendency. Owing to the frequently high molar masses, the substances are relatively slow-reacting and the products cannot be purified by distillation. Therefore, particular demands are made on syntheses with polyalkylene glycols.

It has now been found that, surprisingly, amides can be prepared from polyetheramines and (meth)acrylic acid by using microwaves as an energy source. In this case, the formation of Michael addition products is suppressed, so that the desired amides are obtained in high yield and purity.

The invention thus provides a process for preparing amides of (meth)acrylic acid by mixing a polyetheramine of the formula 1

in which $R^2$ is an organic radical which includes between 2 and 600 alkoxy groups, and $R^3$ is hydrogen or an organic radical having from 1 to 400 carbon atoms with (meth)acrylic acid and irradiating the mixture with microwaves.

$R^2$ contains from 2 to 600 alkoxy groups. In the present context, alkoxy groups are understood to mean a unit of the formula —(AO)— in which A is a $C_2$- to $C_4$-alkylene group. From 2 to 600 alkoxy groups thus mean a structural unit of the formula —(AO)$_n$— where n=from 2 to 600.

In the alkoxy chain represented by (A-O)$_n$, A is preferably an ethylene or propylene radical, in particular an ethylene radical. The total number of alkoxy units is preferably between 5 and 300, in particular between 8 and 200. The alkoxy chain may be a block polymer chain which has alternating blocks of different alkoxy units, preferably ethoxy and propoxy units. It may also be a chain with random sequence of the alkoxy units or a homopolymer.

In a preferred embodiment, —(A-O)$_n$— is an alkoxy chain of the formula 2

$$—(CH_2—CH(CH_3)—O)_a—(CH_2—CH_2—O)_b—(CH_2—CH(CH_3)—O)_c— \qquad (2)$$

in which
a is from 0 to 300, preferably from 0 to 80,
b is from 3 to 300, preferably from 3 to 200,
c is from 0 to 300, preferably from 0 to 80.

$R^3$ is hydrogen or an organic radical having from 1 to 400 carbon atoms. In addition to carbon and hydrogen, $R^3$ may also contain heteroatoms such as oxygen, nitrogen, phosphorus or sulfur.

In a preferred embodiment, $R^3$ is hydrogen, an alkyl radical having from 1 to 50 carbon atoms, an alkenyl radical having from 2 to 50 carbon atoms, an aryl radical having from 6 to 50 carbon atoms or an alkylaryl radical having from 7 to 50 carbon atoms.

In a further preferred embodiment, $R^3$ corresponds to the same definition as $R^2$.

In a further preferred embodiment, $R^3$ contains amino groups. In that case, $R^3$ preferably corresponds to the formula 3

in which $R^4$ may be a divalent hydrocarbon group having from 1 to 50 carbon atoms and $R^5$ and $R^6$ may each be hydrogen or a monovalent hydrocarbon group having from 1 to 50 carbon atoms, where each of $R^4$, $R^5$ and $R^6$ may include from 1 to 200 alkoxy groups and may also contain heteroatoms such as oxygen, nitrogen, phosphorus or sulfur (basically like $R^3$), and m is from 1 to 10.

The products obtained from a monoamine in the process according to the invention correspond to the formula 4

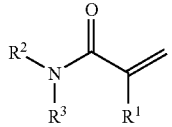
(4)

in which $R^2$ and $R^3$ are each as defined above and $R^1$ is hydrogen or methyl.

When the polyetheramine is a diamine of the formula 5

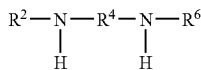
(5)

the product obtained by the process according to the invention corresponds to the formula 6

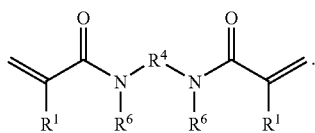
(6)

Correspondingly, it is possible to prepare tri-, tetra- or penta(meth)acrylamides from tri-, tetra- or pentafunctional amines. This gives rise, for example, to a structure of the formula 7

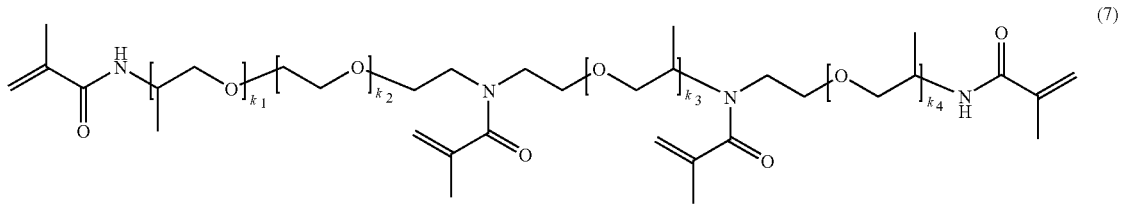
(7)

in which $k_1$, $k_2$, $k_3$ and $k_4$ are each integers which add up to a total of up to 600.

In a further preferred embodiment, the amine of the formula (1) is a polyamine of the formula 8

$$R^7(NHR^8)_n \qquad (8)$$

in which $R^7$ is an n-valent organic radical having from 2 to 400 carbon atoms and may also contain heteroatoms such as oxygen, nitrogen, phosphorus or sulfur, $R^8$ is a radical like $R^3$ and n is an integer from 2 to 20.

When $R^7$ is alkoxylated glycerol, the product of the process according to the invention may, for example, have the following structure:

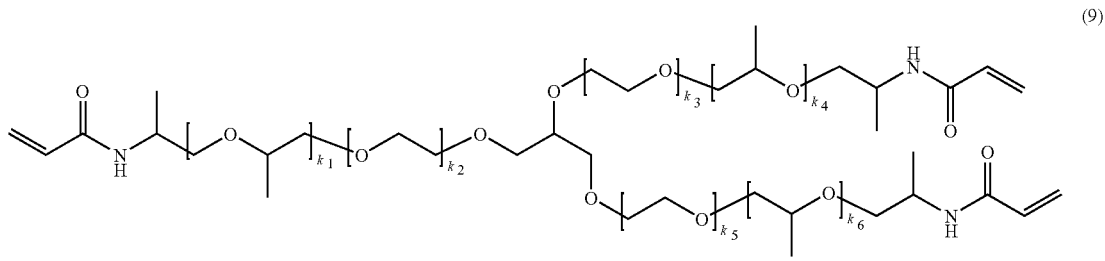
(9)

in which the indices $k_n$ are integers which add up to a total of up to 600.

The polyetheramines used may be mono- or polyfunctional amines which may be branched, unbranched or cyclic, saturated or unsaturated. Such amines are, for example, monofunctional amines, for example alkylpolyalkylene glycol amines, for example methyltriethylene glycol amine, bis(methyltriethylene glycol) amine, butyltriethylene glycol amine, laurylpolypropylene glycol amine, methyltripropylene glycol amine, phenolpolypropylene glycol amine, isotridecylpolypropylene glycol amine, bis(methyltripropylene glycol) amine, N-methylmethylpolypropylene glycol amine, methylpolypropylene glycol amine, bis(methylpolypropylene glycol) amine, methylpolyalkylene glycol amine with random or block-like distribution of the ethylene glycol and propylene glycol units, difunctional amines, for example triethylene glycol diamine, tripropylene glycol diamine, polyethylene glycol diamines, polypropylene glycol diamine, polyalkylene glycol diamine with random or block-like distribution of the ethylene glycol and propylene glycol units, butanediol polyalkylene glycol diamine, resorcinol polyalkylene glycol diamine, trifunctional amines, for example glycerol polyalkylene glycol triamine with random or block-like distribution of the ethylene glycol and propylene glycol units, bis(triethylene glycol amine) amine, bis(polyalkylene glycol amine) amine, tetrafunctional amines, for example pentaerythritol polyalkylene glycol with random or block-like distribution of the ethylene glycol and propylene glycol units,N,N'-bis(polypropylene glycol amine) polyalkylene glycol diamine.

The molar amine:(meth)acrylic acid ratio is preferably in the range of 1:0.2 to 15, in particular in the range of 1:0.8 to 15.

To prevent polymerization during the amidation reaction, the stabilizers known in the prior art may be used. Typical stabilizers are N-oxyls, for example 4-hydroxy-2,2,6,6-tetramethyl-1-oxylpiperidine, 4-oxo-2,2,6,6-tetramethylpiperidine N-oxyl, phenols and naphthols, for example hydroquinone, naphthoquinone, p-aminophenol, p-nitrosophenol, 2-tert-butylphenol, 4-tert-butylphenol, 2,4-di-tert-butylphenol, 2-methyl-4-tert-butylphenol, 4-methyl-2,3-di-tert-butylphenol, Ionol K 65®, p-methoxyphenol, butylhydroxyanisole or 4-amines, for example N,N-diphenylamine, phenylenediamines, for example N,N'-dialkyl-para-phenylenediamines, where the alkyl radicals may be the same or different, hydroxylamines, for example N,N-diethylhydroxylamine, phosphorus compounds, for example triphenylphosphine, triphenyl phosphite or triethyl phosphite, or sulfur compounds, for example sulfur dioxide, diphenyl sulfide, phenothiazine or 5-tert-butyl-4-hydroxy-2-methylphenyl sulfide, and also Irganox® types, Cupferron types® and copper salts.

These compounds may be used individually or in mixtures. The amounts range from 10 ppm to 5% by weight, usually from 50 ppm to 3% by weight, based on the amine used. The reaction may be performed in an inert gas atmosphere (for example nitrogen, argon, helium) or else optionally with addition of air or oxygenous gas mixtures.

The amidation may be performed without or with catalysts. The catalysts known in the prior art may be used here. Typical catalysts are sulfuric acid, sulfurous acid, disulfuric acid, polysulfuric acids, sulfur trioxide, methanesulfonic acid, benzenesulfonic acid, $C_1$-$C_{30}$-alkylbenzenesulfonic acid, naphthalenesulfonic acid, sulfuric monoesters of $C_1$-$C_{30}$-alcohols such as dodecyl sulfate, phosphoric acid, phosphorous acid, hypophosphorous acid, polyphosphoric acid, phosphoric esters of $C_1$-$C_{30}$-alcohols, hydrochloric acid, perchloric acid, acidic ion exchangers, heteropolyacids, solid superacids, and also salts of these acids, Lewis acids such as boron trichloride, aluminum sulfate and iron trichloride.

The catalyst is optionally used in amounts of preferably from 0.01 to 10% by weight, in particular from 0.05 to 5% by weight, based on the overall reaction mixture.

The amidations may be performed at temperatures of from 40 to 250° C. Preference is given to working within the range from 80 to 210° C. The amidation is preferably carried out with an excess of (meth)acrylic acid. Preference is given to working in a pressure range of from 1 mbar to 10 bar.

The amidation may be performed continuously or batchwise.

The amidation is preferably performed without solvent. However, it is also possible to use solvents.

To generate the microwaves, the methods and apparatus customary in industry may be used. Typically, the frequency of the microwaves is in the range between 300 MHz and 300 GHz, which corresponds to a wavelength of from 1 m to 1 mm. Typically, frequencies in the range of 850-950 or 2300-2600 MHz are used, since these frequencies are not used for communication purposes. The microwaves can be transferred to the reaction medium by the known methods. Thus, both multimode and monomode instruments may be used.

EXAMPLES

For examples 1 to 5, a "discover" microwave generator from CEM was used.

For examples 6 to 8, an "MLS-ETHOSplus" microwave instrument from MLS was used.

For comparative example 1, a conventional oilbath was used as the heat source.

Example 1

1 g of a methylpolyalkylene glycol amine (ethylene glycol/propylene glycol mixture) with a mean molar mass of 750 g/mol and 0.34 g of methacrylic acid were charged into a pressure vessel with stirrer bar. The pressure vessel was sealed tightly and the reaction mixture was irradiated at 290 W for 10 minutes with stirring and air cooling in such a way that the maximum temperature was approx. 210° C. Integration by means of $^1$H NMR spectroscopy determined a degree of conversion of >98%.

Example 2

1 g of a methylpolyalkylene glycol amine (ethylene glycol/propylene glycol mixture) with a mean molar mass of 1250 g/mol and 0.4 g of methacrylic acid were charged into a pressure vessel with stirrer bar. The pressure vessel was sealed tightly and the reaction mixture was irradiated at 290 W for 10 minutes with stirring and air cooling in such a way that the maximum temperature was approx. 170° C. Integration by means of $^1$H NMR spectroscopy determined a degree of conversion of >98%.

Example 3

1 g of a methylpolyalkylene glycol amine (ethylene glycol/propylene glycol mixture) with a mean molar mass of 2000 g/mol and 0.2 g of methacrylic acid were charged into a pressure vessel with stirrer bar. The pressure vessel was sealed tightly and the reaction mixture was irradiated at 290 W for 10 minutes with stirring and air cooling in such a way that the maximum temperature was approx. 160° C. Integration by means of $^1$H NMR spectroscopy determined a degree of conversion of >98%.

Example 4

1 g of a glycerol-based polyalkylene glycol triamine (ethylene glycol/propylene glycol mixture) with a mean molar mass of 2500 g/mol and 0.6 g of methacrylic acid were charged into a pressure vessel with stirrer bar. The pressure vessel was sealed tightly and the reaction mixture was irradiated at 290° C. for 10 minutes with stirring and air cooling in such a way that the maximum temperature was approx. 180° C. Integration by means of $^1$H NMR spectroscopy determined a degree of conversion of >98%.

Example 5

20 g of a methylpolyalkylene glycol amine (ethylene glycol/propylene glycol mixture) with a mean molar mass of 1000 g/mol and 10.4 g of methacrylic acid were charged into a pressure vessel with a stirrer bar. The pressure vessel was sealed tightly and the reaction mixture was irradiated at 300 W for 40 minutes with stirring and air cooling in such a way that the maximum temperature did not exceed 200° C. For purification, the reaction solution was taken up in 50 ml of dichloromethane after the reaction had ended. It was extracted once with 50 ml of a 1 normal HCl solution. The organic phase was washed twice with 50 ml of a cold-saturated $NaHCO_3$ solution and subsequently with water. It was dried over magnesium sulfate and the solvent was removed on a rotary evaporator. The product was characterized by means of infrared (IR) and nuclear magnetic resonance (NMR) spectroscopy, and also by means of mass spectrometry (MALDI-TOF). The yield was 85%.

Example 6

20 g of a methylpolyalkylene glycol amine (ethylene glycol/propylene glycol mixture) having a mean molar mass of 2000 g/mol, 8 mg of phenothiazine, 8 mg of para-methoxyphenol and 4.3 g of methacrylic acid were charged into a pressure vessel made of polytetrafluoroethylene with a stirrer bar. The pressure vessel was sealed tightly and the reaction mixture was irradiated with stirring for 6 hours, in the course of which the radiation output was regulated such that the internal temperature was 200° C.

Integration by means of $^1H$ NMR spectroscopy determined a degree of conversion of >90%.

Example 7

25 g of a polyalkylene glycol diamine (ethylene glycol/propylene glycol mixture) having a mean molar mass of 1500 g/mol, 7 mg of phenothiazine, 7 mg of para-methoxyphenol and 11.5 g of methacrylic acid were charged into a pressure vessel made of polytetrafluoroethylene with a stirrer bar. The pressure vessel was sealed tightly and the reaction mixture was irradiated with stirring for 6 hours, in the course of which the radiation output was regulated such that the internal temperature was 200° C.

Integration by means of $^1H$ NMR spectroscopy determined a degree of conversion of >92%.

Example 8

30 g of a resorcinol-based polyalkylene glycol diamine (ethylene glycol/propylene glycol mixture) with a mean molar mass of 2300 g/mol, 10 mg of phenothiazine, 10 mg of para-methoxyphenol and 11.2 g of methacrylic acid were charged into a pressure vessel made of polytetrafluoroethylene with a stirrer bar. The pressure vessel was sealed tightly and the reaction mixture was irradiated with stirring for 6 hours, in the course of which the radiation output was regulated in such a way that the internal temperature was 200° C.

Integration by means of $^1H$ NMR spectroscopy determined a degree of conversion of >90%.

Comparative Example 1 (Thermal Heating)

20 g of a methylpolyalkylene glycol amine (ethylene glycol/propylene glycol mixture) with a mean molar mass of 2000 g/mol, 8 mg of phenothiazine, 8 mg of para-methoxyphenol and 4.3 g of methacrylic acid were charged into a pressure vessel made of glass with a stirrer bar. The pressure vessel was sealed tightly and the reaction mixture was heated to 200° C. with stirring. Even before the desired reaction temperature had been attained, the undesired polymerization of the reaction mixture set in.

What is claimed is:

1. A process for preparing amides of (meth)acrylic acid in an amidation reaction by mixing a polyetheramine of the formula 1

in which $R^2$ is an organic radical which includes between 2 and 600 alkoxy groups, and $R^3$ is hydrogen or an organic radical having from 1 to 400 carbon atoms with (meth)acrylic acid and irradiating the mixture with microwaves.

2. The process as claimed in claim 1, in which $R^3$ is selected from the group consisting of hydrogen, an alkyl radical having from 1 to 50 carbon atoms, an alkenyl radical having from 2 to 50 carbon atoms, an aryl radical having from 6 to 50 carbon atoms, and an alkylaryl radical having from 7 to 50 carbon atoms.

3. The process as claimed in claim 1, in which $R^3$ is an organic radical having between 2 and 600 alkoxy groups.

4. The process of claim 1, in which $R^3$ contains a nitrogen atom.

5. The process of claim 1, in which $R^3$ corresponds to the formula 3

in which $R^4$ is a divalent hydrocarbon group having from 1 to 50 carbon atoms and $R^5$ and $R^6$ are each hydrogen or a monovalent hydrocarbon group having from 1 to 50 carbon atoms, where each of $R^4$, $R^5$ and $R^6$ has from 1 to 200 alkoxy groups, and m is from 1 to 10.

6. A process for preparing amides of (meth)acrylic acid in an amidation reaction by mixing a polyetheramine of the formula 8

in which $R^7$ is an n-valent organic radical having from 2 to 400 carbon atoms, $R^8$ is hydrogen or an organic radical having from 1 to 400 atoms and n is an integer from 2 to 20 with (meth)acrylic acid irradiating the mixture with microwaves.

7. The process of claim 1, in which the molar ratio of the polyetheramine:(meth)acrylic acid is in the range of 1:0.2 to 15.

8. The process of claim 1, in which the amidation reaction is performed at a temperature of from 40 to 250° C.

* * * * *